United States Patent [19]

Gregory et al.

[11] Patent Number: 5,079,381

[45] Date of Patent: Jan. 7, 1992

[54] METHOD FOR THE PREPARATION OF 4-METHYLSULFONYL BENZOIC ACID DERIVATIVES AND INTERMEDIATES

[75] Inventors: Julian A. Gregory; William L. Dehany, both of Huddersfield, England

[73] Assignee: Imperial Chemical Industries PLC, London, England

[21] Appl. No.: 590,115

[22] Filed: Sep. 28, 1990

[51] Int. Cl.$^5$ ............ C07C 253/30; C07C 255/50; C07C 315/02; C07C 317/14
[52] U.S. Cl. .................................. 558/413; 560/11; 560/17; 560/20; 560/22; 562/429; 562/430
[58] Field of Search ............. 560/11, 17, 20, 22; 558/413; 562/429, 430

[56] References Cited

U.S. PATENT DOCUMENTS 4,692,545 9/1987 Carter ........................ 560/18
4,704,467 11/1987 Wehrenberg ................ 560/11

FOREIGN PATENT DOCUMENTS 2445529 4/1976 Fed. Rep. of Germany .

*Primary Examiner*—Jose G. Dees
*Assistant Examiner*—Vera C. Clarke
*Attorney, Agent, or Firm*—Edwin H. Baker

[57] ABSTRACT

This invention relates to an improved process for preparing an herbicidal intermediate compound having the structural formula:

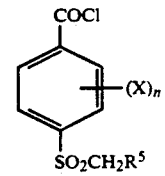

wherein groups X are independently selected from alkyl, haloalkyl, CN, halo, alkoxy, nitro, or $S(O)_mR^2$ where $R^2$ is alkyl and m is 0, 1 or 2, n is 0 or an integer of from 1 to 4 and $R^5$ is hydrogen or $C_{1-6}$ alkyl and intermediate compounds.

4 Claims, No Drawings

METHOD FOR THE PREPARATION OF 4-METHYLSULFONYL BENZOIC ACID DERIVATIVES AND INTERMEDIATES

BACKGROUND OF THE INVENTION

The compounds 2-(chloro, bromo, nitro or methyl)-4-methylsulfonyl-benzoic acid are intermediates that are useful in the preparation of a class of herbicidal compounds including 2-(2'-chloro-4'-methylsulfonyl)-benzoyl-1, 3-cyclohexanedione. These herbicidal compounds and their preparation from the acid chloride or acid cyanide of the above 2-(chloro, bromo, nitro or methyl)-4-methylsulfonyl benzoic acid and a substituted or unsubstituted 1,3-cyclohexanedione are described in several patents including U.S. Pat. No. 4,780,127.

U.S. Pat. No. 4,692,545 teaches a method of preparing compounds having the structural formula:

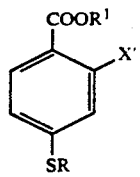

wherein X' is chlorine, bromine, or nitro and R and $R^1$ are alkyl by reacting a compound having the structural formula:

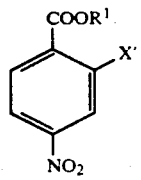

wherein X' and $R^1$ are as defined with an alkyl mercaptan (R—SH) including methyl mercaptan in the presence of an inorganic base and a polar aprotic solvent.

U.S. Pat. No. 4,704,467 teaches an indentical reaction except that it is run in the presence of an inorganic base and a phase transfer catalyst and a non-polar aprotic solvent. The alkyl esters of 2-(chloro, bromo or nitro)-4-methyl thiobenzoic acid are easily oxidized to the corresponding alkyl ester of 2-chloro-4-methylsulfonyl benzoic acid by conventional techniques.

The esters of 2-(chloro, bromo, or nitro)-4-methylthiobenzoic acid are converted to the corresponding benzoic acids by known techniques.

SUMMARY OF THE INVENTION

One embodiment of this invention relates to an improved process for preparing an herbicidal intermediate compound having the structural formula:

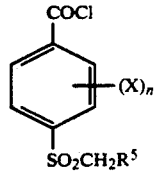

wherein groups X are independently selected from alkyl, haloalkyl, CN, halo, alkoxy, nitro, or $S(O)_m R^2$ where $R^2$ is alkyl and m is 0, 1 or 2, n is 0 or an integer of from 1 to 4 and $R^5$ is hydrogen or $C_{1-6}$ alkyl by the following multi-step reaction scheme:

Step (1) procurement by conventional means or purchase of a substituted benzoic acid of the structural formula:

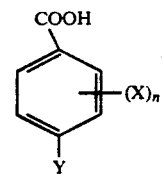

wherein X and n are as hereinbefore defined and Y is a leaving group such as nitro or halo for example chloro.

Step (2) reacting the substituted benzoic acid of Step (1) with a hydrocarbyl alcohol, such as $C_{1-10}$ alkyl alcohol, $C_{2-10}$ alkenyl or alkynyl alcohol or aralky alcohol of up to 10 carbon atoms. Examples of alcohols are methanol, ethanol, butanol, benzylalcohol or iso-octyl alcohol. Preferably the alcohol is butanol. The reaction is suitably effected in the presence of a catalyst preferably an acid, such as sulphuric acid, toluene sulphonic acid, hydrochloric acid or O-phosphoric acid, or a Lewis acid such as aluminium trichloride or an ion-exchange resin. The reaction is optionally effected in the presence of a solvent, for example the alcohol may also serve as a solvent for the reaction. A cosolvent may be employed if desired and suitable cosolvents are those which are capable of azeotroping water at temperatures up to 140° C. such as toluene, xylene, monochlorobenzene or other hydrocarbon solvents.

Step (3) reacting the ester of Step 2 which has the structural formula:

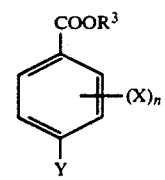

wherein X, Y, and n are as defined and $R^3$ is a hydrocarbyl group with an ester of thioglycolic acid having the structural formula $HS\text{-}CHR^5COOR^4$ wherein $R^4$ is a hydrocarbyl group and $R^5$ is hydrogen or $C_{1-6}$ alkyl in the presence of a base to form a diester having the structural formula

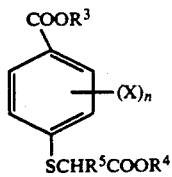

wherein X, n, $R^3$, $R^4$ and $R^5$ are as defined. Suitable groups $R^3$ and $R^4$ are straight or branched $C_{1-10}$ alkyl, $C_{2-10}$ alkenyl, $C_{2-10}$ alkynyl or aralkyl groups of up to 10 carbon atoms. Suitable bases include alkali metal carbonates or hydroxides such as potassium carbonate, sodium cacrbonate, potassium hydroxide or sodium hydroxide. A preferred base is potassium carbonate.

Carrying out in any order an oxidation step and a de-esterfication steps. Therefore either:

Step 4a reacting the diester of step 3 with an inorganic base such as sodium or potassium hydroxide to form a disalt, or an acid such as sulphuric acid or p-toluene-sulphonic acid to form a diacid, the product being of formula:

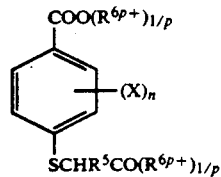

where $R^6$ is hydrogen and p is 1 or $R^6$ a cation of charge p such as alkali metal ion for example sodium or potassium or alkaline earth metal such as calcium or magnesium; and Step 5A oxidising the disalt or diacid of step 4a and heating to form a substituted benzoic acid of formula:

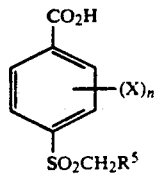

where $R^5$, X and n are as defined; or

Step 4b oxidising the diester of step (3) to form a compound of formula:

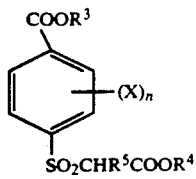

where $R^3$, $R^4$, $R^5$ X and n are as defined; and

Step 5b reacting the product of Step 4b with base such as sodium hydroxide in an aqueous solution followed by heating to form the compound of formula:

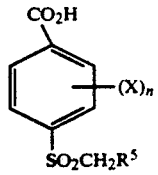

where $R^5$ and n are as hereinbefore defined.

Step (6) the substituted benzoic acid of Step 5a and 5b is converted to the corresponding di-substituted benzoyl chloride by conventional techniques such as reaction with oxalyl chloride.

Steps (1) and (2) above are optional and any route or source can be employed to obtain the ester for use in Step 3.

If desired the ester HS-CHR$^5$COOR$^4$ used in Step 3 can be prepared in situ in Step 2 from the corresponding acid.

The products of Step 4a, 4b, 5a and 5b are novel and as such form a further aspect of the invention. Hence in a further aspect of the invention there is provided a compound of formula (II):

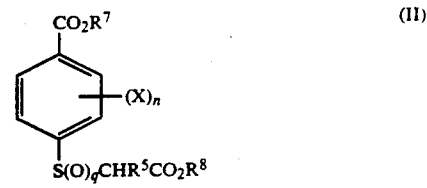

where X, n and $R^5$ are as hereinbefore defined, q is 0, 1 or 2, $R^7$ and $R^8$ are independently selected from hydrogen, a cation or a hydrocarbyl group.

Suitable hydrocarbyl groups $R^7$ and $R^8$ include those defined before for $R^3$ and $R^4$. Compounds of formula (II) where q is 1 can be prepared by carrying out partial oxidation only in step 4(a) or 5(b) and isolating the desired product.

Preferably n is 1 and X is at the 2 position on the ring. Suitable alkyl and alkoxy groups x and $R^2$ are those containing from 1 to 4 carbon atoms. Suitable halo groups X are chloride and bromine. Suitable haloalkyl groups include trifluoromethyl.

Preferably X is selected from chlorine, bromine, nitro or methyl.

Preferably $R^5$ is hydrogen.

The improved process of this invention can be easily understood by referring to the following reaction scheme which shows one embodiment of the invention and considering the detailed description of the invention.

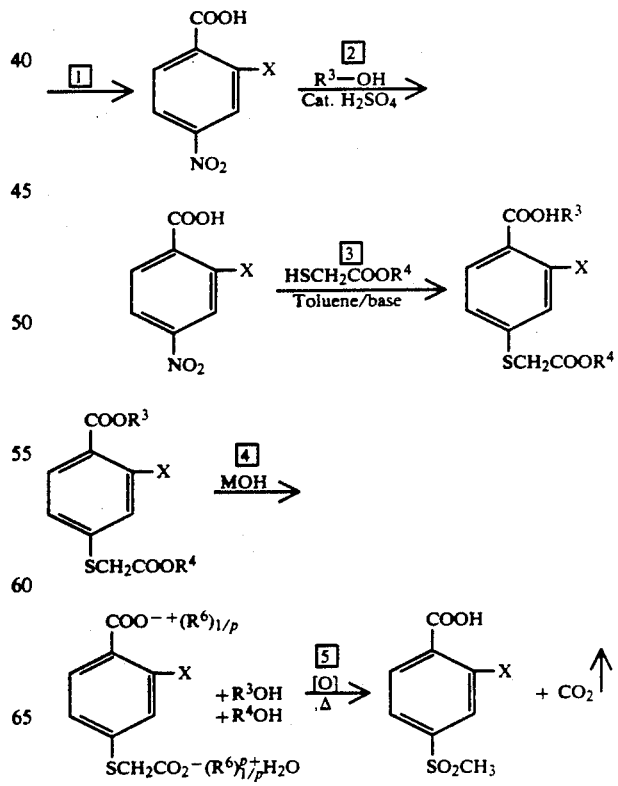

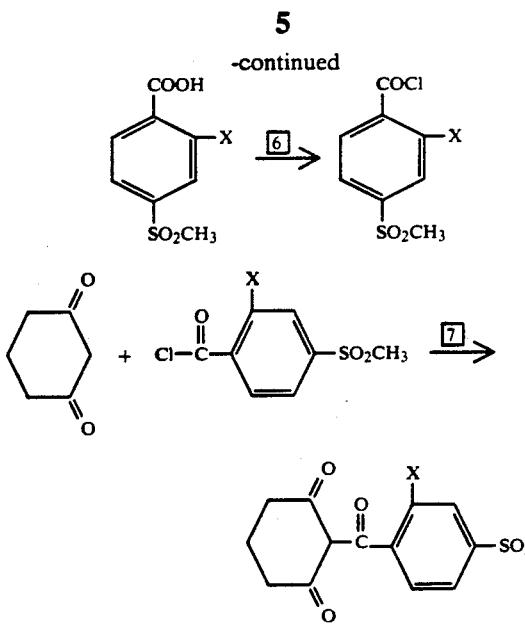

DETAILED DESCRIPTION OF THE INVENTION

In reaction Step 2, the substituted benzoic acid can be esterified by conventional techniques. Preferably the alcohol has 3 to 6 carbon atoms. Most preferably the alcohol is n-butanol and the esterification reaction is run in the presence of a catalyst such as sulfuric acid. Preferably the reaction is run with azeotropic water removal at reflux temperature until complete. The reaction can be run in a solvent such as toluene, xylene, monochlorobenzene or other hydrocarbon solvents, However, the alcohol may also serve as the solvent for the reaction. The ester reaction product can be recovered by conventional techniques.

In reaction Step 3, the leaving group of the ester of 4-substituted-benzoic acid is displaced by an alkyl ester of thioglycolic acid as defined. Preferably the n-butyl ester is used.

The reaction can be run in a non-aqueous medium in the presence of an inorganic base, preferably the base is finely divided if a solid and preferably is potassium hydroxide, potassium carbonate, sodium carbonate, sodium hydroxide, tripotassium phosphate or trisodium phosphate.

A non-aqueous medium includes the two reactants with no additional solvent.

If a solvent is required, preferably an aprotic one should be used. Aprotic solvents have no exchangeable hydrogen atom such as are found in hydroxy, mercaptan or amine groups.

If the aprotic solvent is polar, then the presence of a phase transfer agent is not necessary. If it is non-polar, then a phase transfer agent is necessary.

Non-polar aprotic solvents include hydrocarbons such as benzene, toluene, xylenes; halogentated hydrocarbons such as dichloromethane, 1,2-dichloroethane, chlorobenzene; ethers such as tetrahydrofuran, diethyl ether, diisobutyl ether and other non-polar aprotic solvents. Polar aprotic solvents include acetone, methyl ethyl ketone, acetonitrile, dimethylformamide, N-methyl pyrrolidone, dimethylacetamide and methyl isobutyl ketone. Phase transfer catalysts are well known and include tris-(3,7-dioxaheptyl)amine (TDA-1), tricaprylyl-methylammonium chloride (Aliquat 336), tetra-lower alkyl substituted ammonium, phosphonium, sulfonium and sulfoxonium halides, crown ethers and cripates. Particular examples are tetrabutyl ammonium bromide and tetraphenylphosphonium bromide.

The term 'lower alkyl' includes $C_{1-6}$ alkyl groups.

A two-phase system can be used if desired and is preferred. In this system one phase contains the two reactants and the desired product as it is prepared. This phase can be considered a solvent. The other phase is an aqueous phase containing the dissolved inorganic base. In this system, a phase transfer catalyst is required to allow reaction.

In Step 4a, the diester reaction product of reaction Step 3, which has the structural formula:

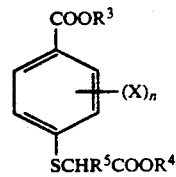

wherein X, n, $R^3$ and $R^4$ and $R^5$ are as defined is hydrolysed to the disalt by reaction with two mol of a base such as potassium or sodium, hydroxide with two mol of alcohol being formed ($R^3OH + R^4OH$). The reaction is run in water at reflux temperature for example of from 80°-120° C. preferably about 105° C. for 2-8 hours. The reaction product need not be recovered but is carried forward to the next reaction step as an aqueous solution or suspension of the disalt or diacid.

In reaction Step 5a, a mol amount of the disalt or diacid of reaction Step 4a is adjusted to a pH of from 2 to 10 preferably from 4 to 5 by addition of acid such as sulphuric acid or base such as sodium hydroxide. The product which has the structural formula:

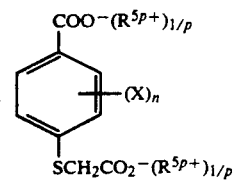

is oxidized with at least 2 moles of an oxidizing agent such as a peroxide for example hydrogen peroxide in water. The reaction is preferably carried out in the presence of a catalyst such as sodium tungstate, tungsten trioxide, sodium orthovanadate, ammonium metavanadate, tungstic acid or molybdic acid at a temperature of between about 40° to about 80° C., preferably at about 60° C. The resultant hydroxycarbonylmethylsulphone group or its metal salt on the 4 position can be decarboxylated liberating carbon dioxide and yielding an alkylsulfone moiety by heating to a reflux temperature to yield the product:

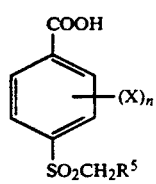

wherein X and n are as defined.

In reaction Step 4(b), conventional oxidising conditions are suitably employed. Suitable oxidising agents include hydrogen peroxide and formic acid, or a peracid such as peracetic acid. An organic solvent such as toluene is suitably employed and the reaction is carried out at elevated temperature for example of from 50°-100° C. preferably about 75° C.

As for reaction Step 5(b), the conditions employed are broadly similar to those described in relation to Step 4(a).

In reaction Step 6, the substituted benzoic acid product of reaction Step 5a or 5b is converted to its acid chloride by reaction with oxalyl chloride according to the teaching of Reagents for Organic Synthesis, Vol. 1, L. F. Fieser and M. Fieser, pp 767-769 (1967).

The process of this invention can be better understood by reference to the following examples.

EXAMPLE 1

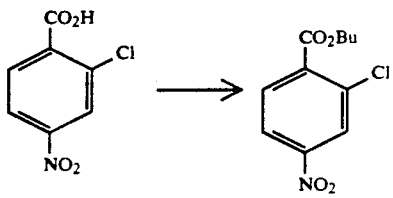

2-Chloro-4-nitrobenzoic acid (1000.0 g, 4.93 mol) was dissolved in butanol (747.0 g, 10.10 mol) with stirring sulphuric acid (9.7 g, 0.10 mol) was added and the reaction heated to reflux under Dean-Stark conditions for 6 hours, when no more water was seen to collect in the butanol/water separater.

The reaction was allowed to cool to 50° C. and washed with aqueous potassium carbonate solution ($K_2CO_3$ 27.2 g, 0 2 mol; $H_2O$ 595 g). The organic layer was separated off and the solvent removed under reduced pressure at 125° C. and 100 mm Hg to remove excess butanol, to yield the desired butyl ester (1257.0 g).

EXAMPLE 2

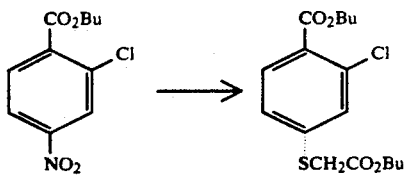

An aqueous solution of potassium carbonate ($K_2CO_3$ 288.0 g 2.08 mol, $H_2O$ 385 g) was added dropwise over 1 hour to a stirred mixture of the product of example 1 (500.0 g, 1.84 mol), butylthioglycolate (307.3 g, 1.97 mol) and tetrabutyl- ammonium bromide (14.9 g, 0.05 mol) keeping the temperature below 30° C. The reaction was stirred for a further 1 hour, at ambient temperature, then heated to 50° C. and stirred for a further 1 hour.

Water (250 g) was added dropwise maintaining the reaction temperature at 50° C. with stirring. The reaction was allowed to settle and the organic layer separated. The organic layer was washed with aqueous sulphuric acid ($H_2SO_4$ 23.5 g, 0.24 mol; $H_2O$ 436 g) and separated to yield the stage 3 dibutyl ester product (717.5 g).

EXAMPLE 3

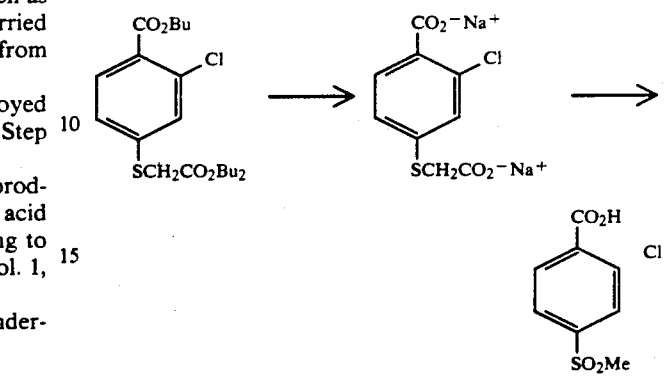

Aqueous sodium hydroxide (NaOH, 106.6 g, 0.72 mol;) was added dropwise over 1 hour to a stirred suspension of the product of Example 2(100.0 g, 0.24 mol) and water (54.0 g) at 90° C. During the course of the addition the reaction was heated to reflux under Dean-Stark conditions separating off the liberated butanol. The reaction was maintained at reflux for a further 6 hours until no more butanol was seen to collect in the butanol/water separater. At this point water (20 g) was distilled off the reaction to complete butanol removal. The reaction was allowed to cool to 60° C. and water (88.4 g) added, the reaction temperature was adjusted to 60° C. and sodium tungstate (0.53 g, 0.002 mol) added followed by the dropwise addition of sulphuric acid (10.4 g, 0.11 mol) while maintaining the reaction temperature at 60° C.

Hydrogen peroxide (63.8 g, 0.56 mol) was added to the reaction over 2 hours maintaining the reaction at 60° C. and then stirred for a further 1 hour at 60° C.

Sulphuric acid (10.4 g, 0.11 mol) was added dropwise to the reaction maintaining the reaction temperature at 60° C. On completion of the addition the reaction was heated to reflux for 10 hours.

The reaction was allowed to cool to 60° C. and sulphuric acid (14.3 g, 0.15 mol) added dropwise over 30 minutes. The reaction was allowed to cool to 35° C. and the precipitate filtered off and washed with water (67 g) at 50° C. The solid was dried under vacuum at 80° C. for 12 hours to yield the desired 2-chloro-6-methylsulphonyl-benzoic acid (52.5 g).

EXAMPLE 4

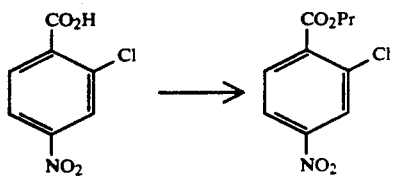

2-Chloro-4-nitrobenzoic acid (200.0 g, 0.98 mol) was dissolved in toluene (520 g) and propanol (125.8 g, 2.1 mol). Sulphuric acid (2.6 g, 0.05 mol) was added and the reaction heated to reflux under Dean-Stark conditions for 7 hours, when no more water was seen to collect in the toluene/water separator.

The reaction was allowed to cool to room temperature and washed with aqueous sodium bicarbonate solution (NaHCO₃, 69.0 g, 0.81 mol; H₂O 620 g). The organic layer was separated off and azeotropically dried to yield a toluene solution of the propyl ester.

EXAMPLE 5

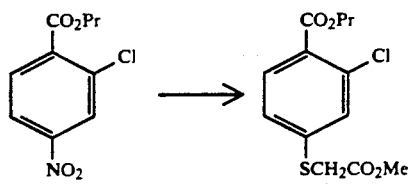

Potassium carbonate (176.1 g, 1.27 mol) was added to a stirred solution of the product of example 4 (267.7 g, 0.93 mol) in acetone (660 g), and the reaction heated to 55° C.

Methyl thioglycolate (135.0 g, 1.2 mol) was added to the reaction at 55° C. over 2 hours, then the reaction maintained at reflux for 6 hours.

Acetone was distilled from the reaction, upto a maximum reaction temperature of 70° C. The reaction mass was diluted with toluene (770.0 g) and water (1500.0 g). The reaction was neutralised by the addition of sulphuric acid (25.0 g, 0.25 mol), heated to 50° C. and allowed to settle.

The organic layer was separated off, to give a toluene solution of the diester product.

EXAMPLE 6

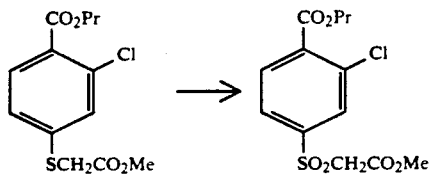

Formic acid (11.5 g, 0.22 Mol) was added to a toluene solution of the product of example 5 (285 ml, ca 0.2 Mol) and the reaction heated to 75° C. Hydrogen peroxide (23.2 g, 0.2 Mol) was added over 30 minutes to the vigorously stirred reaction, maintaining the temperature at 75° C. On completion of the addition two further peroxide charges were added, each over 30 mins. On completion of the third addition the reaction was maintained at 75° C. for 4 hours.

The reaction was diluted with water (95 g) and allowed to cool to 30° C., and excess peroxide reduced by addition of aqueous 10% sodium sulphite solution. The reaction was neutralised to pH 6.5-7.0 by the addition of aqueous sodium hydroxide (17.4 g, 0.2 Mol). The organic layer was separated off to give a toluene solution of the sulphone product.

EXAMPLE 7

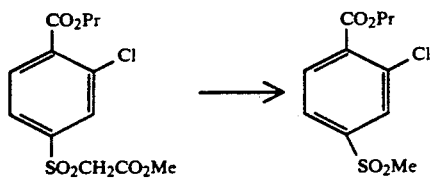

Water (350 g) and aqueous sodium hydroxide solution (43.4 g, 0.51 Mol) were added to a stirred solution of the product of Example 6 in toluene (285 ml, ca 0.175 Mol). The reaction was heated to reflux and the toluene azeotropically distilled off, while returning water to the reaction. The reaction was maintained at reflux for 16 hours.

The reaction was cooled to 10° C. and sulphuric acid (25.0 g, 0.26 Mol) added dropwise while maintaining the temperature at 10° C.

The precipitate was filtered off, washed with a little cold water and dried under vacuum at 80° C. for 12 hours to yield 2-chloro-4-methylsulphonylbenzoic acid (34.3 g).

EXAMPLE 8

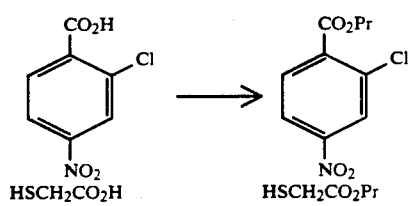

2-chloro-4-nitrobenzoic acid (20.0 g, 0.1 Mol) and thioglycolic acid (10.1 g, 0.1 Mol) were dissolved in toluene (108.7 g) and propanol (26.5 g, 0.045 Mol). Amberlyst A15 resin (15.0 g) was added and the reaction heated to reflux under Dean-Stark condions for 30 hours until no more water was seen to separate in the toluene/water separator.

The reaction was allowed to cool to ambient temperature and washed with aqueous sodium bicarbonate solution (NaHCO₃, 3.5 g; H₂O 100 g). The organic layer was separated off and azeotropically dried.

EXAMPLE 9

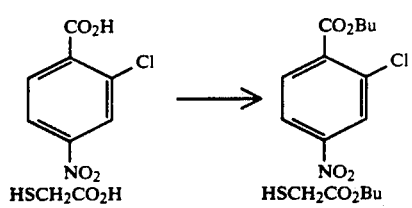

2-chloro-4-nitrobenzoic acid (40.0 g, 0.2 Mol) and thioglycolic acid (21.9 g, 0.24 Mol) were dissolved in butanol (183.1 g, 2.47 Mol). Para-toluene sulphonic acid (20.7 g, 0.11 Mol) was added and the reaction heated to reflux under Dean-Stark conditions for 24 hours, when no more water was seen to separate in the butanol/water separater.

The reaction solution was washed with aqueous sodium bicarbonate solution (NaHCO₃, 9.2 g; H₂O, 150 g) and water (2×100 g). The organic layer was separated and azeotropically dried to give a solution of stage 2 butyl ester and butyl thioglycolate.

EXAMPLE 10

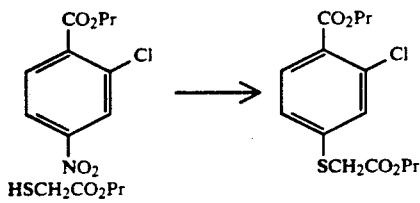

The solvent was removed from a sample of the product from Example 8 under reduced pressure, to leave a mixture of propyl esters; stage 2 propyl ester (ca 0.05 Mol) and propyl thioglycolate (ca 0.055 Mol).

The residue was taken up in acetone (75 ml), heated to 55° C. and potassium carbonate (7.59 g, 0.055 Mol) added. The reaction was stirred at 55° C. for 5 hours.

Toluene (75 ml) was added to the reaction and the acetone removed by distillation under reduced pressure. The reaction solution was diluted with water (80 g) and neutralised with 1N hydrochloric acid (46 ml), and the organic layer separated off to give a toluene solution of the dipropyl ester.

EXAMPLE 11

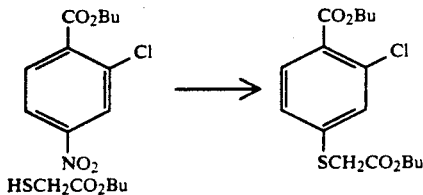

The solvent was removed from a sample of the product of Example 9 under reduced pressure, to leave a mixture of stage 2 butyl ester (ca 0.05 Mol) and butyl thioglycolate (ca 0.05 Mol).

The residue was taken up in acetone (50 ml), heated to 55° C. and potassium carbonate (7.6 g, 0.055 Mol) added. The reaction was stirred for at least 55° C. for 5 hours.

Toluene (75 ml) was added to the reaction and the acetone removed by distillation under reduced pressure. The reaction solution was diluted with water (80 g) and neutralized with 1N hydrochloric acid (46 ml). The organic layer was separated off to give a toluene solution of the dibutyl ester.

EXAMPLE 12

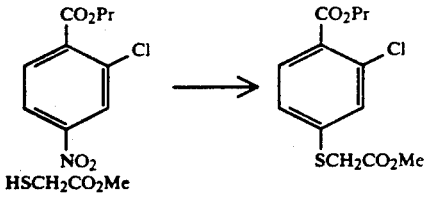

Potassium carbonate (7.6 g, 0.055 Mol, fine grade) and the phase transfer catalyst (0.005 Mol) were added to a toluene solution of the product of Example 1 (40 ml, containing 0.05 Mol) at 50° C.

Methyl thiogylycolate (5.8 g, 0.055 Mol) was added and the temperature adjusted to 55° C. and the reaction stirred for 5 hours.

The reaction was diluted with water (80 g) and neutralised with 1N hydrochloric acid (46ml). The organic layer was separated off to yield a toluene solution of product.

The reaction was carried out using the following as phase transfer catalysts:
TDA-1 (1.6 g)
Me$_4$NBr (0.77 g)
Benzyl triethyl ammonium bromide (1.1 g)
C$_{15}$H$_{34}$Bu$_3$PBr (2.5 g)
Tetrabutyl phosphonium bromide (1.7 g)
Tetraphenylphosphonium bromide (2.1 g)

EXAMPLE 13

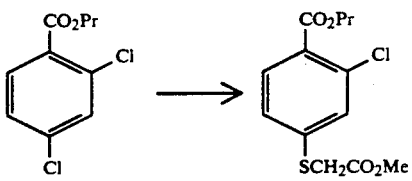

Potassium carbonate (3.1 g, 0.022 Mol) was added to a solution of the propyl 2,4-dichlorobenzoate (5.0 g, 0.02 Mol) in DMF (40ml) and heated to 50° C. A solution of methyl thioglycolate (2.4 g, 0.044 Mol) in DMF (5 ml) was added and the reaction stirred at 50° C. for 10 hours and then at 100° C. for 5 hours.

The reaction was allowed to cool and diluted with water (100 g) and extracted with toluene. The toluene layers were combined and the solvent removed under reduced pressure.

Chromatography of the residue on silica using ethyl acetate: petrol 1:8 as eluant allowed isolation of the product (2.0 g).

We claim:

1. A method for preparing a substituted benzoic acid compound having the structural formula

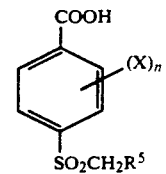

wherein X groups are independently selected from alkyl, halo, haloalkyl, CN, alkoxy, nitro or S(O)$_m$R$^2$ where R$^2$ is alkyl and m is 0, 1 or 2, and n is 0 or an integer of from 1 to 4, and R$^5$ is hydrogen or C$_{1-6}$ alkyl, the process comprising reacting an ester having the structural formula

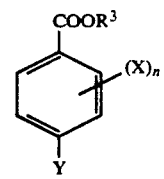

where X, n are as defined, R$^3$ is a hydrocarbyl group and Y is a leaving group and with an alkyl ester of thioglycolic acid having the structural formula HS-CHR$^5$ COOR$^4$ wherein R$^4$ is hydrocarbyl groups and R$^5$ is as defined and in the presence of a catalyst to prepare a substituted benzoic acid ester compound of the structural formula

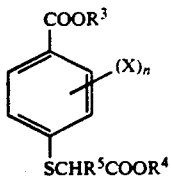

wherein $R^3$, $R^4$, $R^5$ and X are as defined and thereafter in any order carrying out the following steps: (i) oxidising the thio group to a sulphone group and (ii) de-esterfying; and thereafter decarboxylating the sulfone substituent of the product.

2. A method for preparing a disubstituted benzoic acid compound having the structural formula

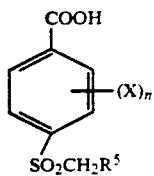

wherein X, n and $R^5$ are as defined in claim 1 comprising reacting an ester having the structural formula:

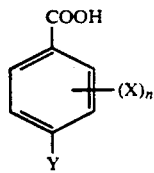

wherein X, n, Y and $R^3$ are as defined in claim 1 with an alkyl ester of thioglycolic acid having the structural formula HS-CHR$^5$COOR$^4$ wherein $R^4$ and $R^5$ are as defined in claim 1 in a solvent and in the presence of a catalyst to prepare a di-substituted benzoic acid ester compound of the structural formula

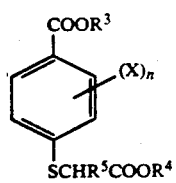

wherein $R^3$, $R^4$, X and n are as defined, followed by reacting the substituted benzoic acid ester with at least two mol of an inorganic base to prepare a disalt of the structural formula

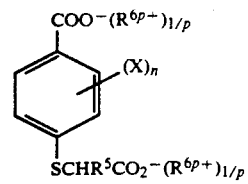

wherein X is as defined and $R^6$ is a cation of charge p, followed by a oxidising and heating the salt to prepare the desired substituted benzoic acid derivative.

3. A compound of formula (II)

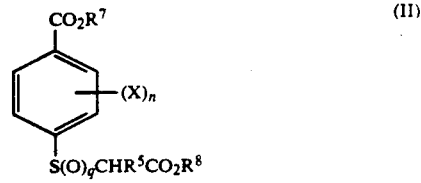

(II)

wherein X groups are independently selected from alkyl, halo, haloalkyl, CN, alkoxy, nitro or $S(O)_m R^2$ where $R^2$ is alkyl and m is 0, 1 or 2; n is 0 or an integer of from 1 to 4; and $R^5$ is hydrogen or $C_{1-6}$ alkyl; q is 0, 1 or 2; and $R^7$ and $R^8$ are independently selected from the group consisting of hydrogen, a cation and a hydrocarbyl group.

4. A method for preparing a disubstituted benzoic acid compound having the structural formula

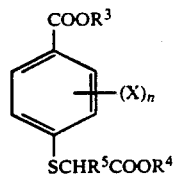

wherein X groups are independently selected from alkyl, halo, haloalkyl, CN, alkoxy, nitro or $S(O)_m R^2$ where $R^2$ is alkyl and m is 0, 1 or 2; n is 0 or an integer of from 1 to 4; $R^3$ and $R^4$ are both hydrocarbyl groups; and $R^5$ is hydrogen or $C_{1-6}$ alkyl comprising reacting an ester having the structural formula

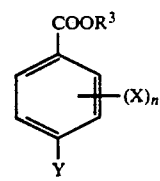

wherein X, n and $R^3$ are as defined and Y is a leaving group with an ester of thioglycolic acid having the structural formula HS-CHR$^5$COOR$^4$ wherein $R^4$ and $R^5$ are as defined in a solvent and in the presence of a catalyst to prepare the desired substituted benzoic acid ester compound of the structural formula

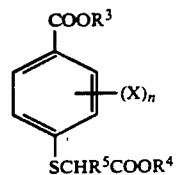

wherein $R^3$, $R^4$, $R^5$, X and n are as defined.

* * * * *